(12) United States Patent
Belfor et al.

(10) Patent No.: US 7,314,372 B2
(45) Date of Patent: *Jan. 1, 2008

(54) SYSTEM AND METHOD TO BIOENGINEER FACIAL FORM IN ADULTS

(75) Inventors: Theodore Belfor, New York, NY (US); Gurdev Dave Singh, San Juan, PR (US)

(73) Assignee: Orthovisage, Inc., Catskill, NY (US)

( * ) Notice: Subject to any disclaimer, the term of this patent is extended or adjusted under 35 U.S.C. 154(b) by 180 days.

This patent is subject to a terminal disclaimer.

(21) Appl. No.: 10/849,713

(22) Filed: May 19, 2004

(65) Prior Publication Data

US 2005/0261679 A1 Nov. 24, 2005

(51) Int. Cl.
*A61C 7/00* (2006.01)
(52) U.S. Cl. .............................. 433/24; 433/7; 433/18
(58) Field of Classification Search .................. 433/7, 433/18, 19, 21, 24
See application file for complete search history.

(56) References Cited

U.S. PATENT DOCUMENTS

| | | | | |
|---|---|---|---|---|
| 4,026,023 | A | * 5/1977 | Fisher | 433/7 |
| 4,239,487 | A | * 12/1980 | Murdock | 433/7 |
| 4,433,956 | A | * 2/1984 | Witzig | 433/7 |
| 4,439,149 | A | 3/1984 | Devincenzo | |
| 4,457,708 | A | 7/1984 | Dufour | |
| 4,609,349 | A | * 9/1986 | Cain | 433/6 |
| 5,002,485 | A | * 3/1991 | Aagesen | 433/7 |
| 5,163,840 | A | 11/1992 | Bourke | |
| 5,324,196 | A | 6/1994 | Magill | |
| 5,443,384 | A | 8/1995 | Franseen et al. | |
| 5,536,168 | A | 7/1996 | Bourke | |
| 5,540,687 | A | * 7/1996 | Fairley et al. | 606/60 |
| 5,795,150 | A | 8/1998 | Boyd | |
| 5,848,981 | A | 12/1998 | Herbranson | |
| 6,096,079 | A | 8/2000 | Eaton | |
| 6,099,304 | A | 8/2000 | Carter | |
| 6,334,771 | B1 | 1/2002 | Liou | |
| 6,435,870 | B1 | 8/2002 | Walde | |

(Continued)

*Primary Examiner*—Cary E. O'Connor
(74) *Attorney, Agent, or Firm*—Hoffman, Warnick & D'Alessandro LLC

(57) ABSTRACT

A method and apparatus are provided for changing the form of the jaw and facial bones of an adult patient that did not develop fully during childhood. The method utilizes a device having a plate body with an expansion screw device that fits within the mouth of the patient, flap springs that project from the plate body and an overlay extending from the plate body. The device is placed within the mouth of the patient so that the overlay is in a position between at least two opposing teeth. In this position the flap springs press against selected teeth that are out of alignment in order to urge those teeth back into place. This force on the teeth causes the jawbone to expand to accept the teeth in their proper position(s). Also, the device is arranged such that the opposing teeth contact the overlay during swallowing, which causes the patient's facial muscles to intermittently pull on the facial bones. This intermittent application of force to the facial bones causes these bones to further develop toward a symmetrical appearance of the face and the positioning of out of place teeth/tooth into proper position. The device can be adjusted by small motors under the control of a microprocessor located on the body plate based on readings from sensors on the flap springs.

26 Claims, 13 Drawing Sheets

U.S. PATENT DOCUMENTS

| | | |
|---|---|---|
| 6,530,375 B1 | 3/2003 | Cieslik, Jr. |
| 6,604,527 B1 | 8/2003 | Palmisano |
| 6,648,639 B2 | 11/2003 | Mao |
| 2002/0072029 A1* | 6/2002 | Mao .......................... 433/24 |
| 2003/0049581 A1* | 3/2003 | DeLuke ........................ 433/7 |
| 2004/0009449 A1 | 1/2004 | Mah |
| 2004/0013993 A1 | 1/2004 | Ito |
| 2005/0186524 A1* | 8/2005 | Abolfathi et al. .............. 433/7 |

* cited by examiner

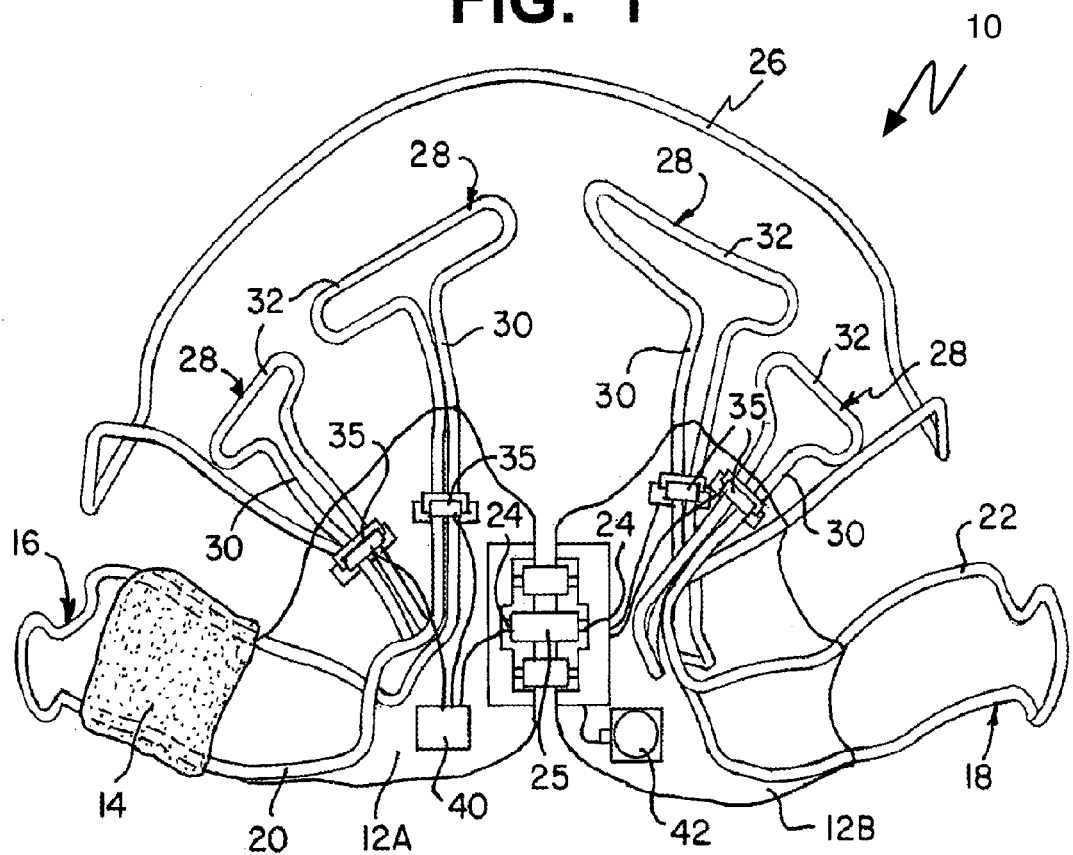

SYSTEM AND METHOD TO BIOENGINEER FACIAL FORM IN ADULTS

BACKGROUND OF THE INVENTION

1. Field of the Invention

The present invention relates to a non-surgical method to enhance facial form and enhance facial symmetry by using an orthodontic dental device or appliance in adults. More specifically, the present invention relates to an orthodontic device that stimulates the muscles of the face and jaws, which in turn stimulate the bone causing a remodeling or reshaping that improves facial symmetry and causes jaw development where jaw development did not occur during childhood.

2. Discussion of the Related Art

Devices have been used for decades to straighten patients' teeth. Patients' teeth may not erupt optimally for a number of reasons, specifically if the jawbone did not fully develop during childhood. Thus, in an underdeveloped jaw there is not sufficient room to accommodate the patient's full set of teeth. Because there is not enough room in the jawbone for all of a patient's teeth, some of these devices first require extraction of one or more teeth to provide room in the patient's jaws for the remaining teeth, so that they may be rotated or otherwise moved into a straighter position.

One conventional device that is used to straighten the alignment of teeth is braces. Braces are used to move teeth, which causes the bone to change locally around the roots of the teeth. Braces do not, however, stimulate the muscles of the face and/or jaws, and, therefore, do not cause any change of the facial or jawbones, except for the local change of the jawbone around the roots of the teeth moved by the braces.

Another device used to straighten the alignment of teeth is a split palate orthodontic appliance such as that disclosed in U.S. Pat. No. 4,026,023 of Fisher. Split palate appliances include a split acrylic body whose two body halves are connected with an expansion screw. The acrylic body rests against the palate of the mouth when the device is placed in the upper jaw, or against the lingual surfaces of the mandible when the device is placed in the lower jaw. Because prior split palate devices contact the palate, they prevent the palate from descending as the palate is widened. T-shaped flap springs, which are also known as Fisher flap springs, are embedded in the plate body. The free edge of each spring makes contact with a selected tooth or teeth to apply a predetermined amount of pressure against that tooth. This pressure slowly causes selective orthodontic movement of the teeth. In particular, the pressure applied by the springs to the teeth slowly decreases due to changes in the palate or mandible due to the pressure. Thus, periodically (once or twice a week) the expansion screw is actuated to further spread apart the two body halves, thereby applying (or more accurately reapplying) more pressure against the respective teeth. As the jaw remodels, however, the widening is usually limited inter alia by sutural homeostasis, a regulatory mechanism that is under genetic control, and modulated in response to function.

Remodeling of bone through force can occur throughout a person's life. It is believed that the bones of some individuals do not fully develop during childhood because of a lack of sufficient stimulation. Primitive man had better-developed jaws, straighter teeth and a wider smile than his modern day descendants, because the food was very tough and a baby would eat the same food as the parents. Modern day babies are reared on soft foods so their jaws do not develop as well. On top of that, changes in feeding behavior and/or environmental pollution narrow the nasal passages of many post-industrial infants. As a result they breathe through their mouth, causing their palate to develop inward instead of outward, and leaving less room for their upper teeth. Not only does this result in crowded and crooked teeth, jaw development (or lack of it) affects the morphology of the face.

There is a direct relationship between facial development and beauty. In every culture of the world, a symmetrical face with high cheekbones, a wide smile and a strong jaw is considered beautiful. Even an infant will respond to a wide beautiful smile with even teeth. Adults also respond to a well-developed face and body as being beautiful.

In the article by Moss, "The role of mechanotransduction," *American Journal of Orthodontics Dentofacial Orthopedics,* 112:8-11 (1997) there is a discussion of the "functional matrix hypothesis." It asserts that a seamless communication takes place when mechanical forces overload the periosteum (tissues around the bone and teeth). In effect there is a combination of mechanical/biochemical communication that takes place all the way down to the individual gene-containing nucleus of the osteocytic cells, i.e., the cells that create bone and direct changes in bone. This communication directly affects the DNA of the genome within the nucleus and creates an interconnected physical chain of molecular levers that affect the periosteal functional matrix activity, which regulates the genomic activity of its strained skeletal unit bone cells, including their phenotypic expression. Thus, the theory is that the strain placed on the bone not only forces the bone to change, but it triggers the genetic encoding of the bone to cause it to continue its earlier arrested development toward a symmetrical facial appearance.

None of the prior art devices directly stimulates the muscles of the face and jaws, which in turn stimulate the bone causing a remodeling or reshaping of the facial and jawbones to improve facial symmetry.

None of the prior art devices causes the jawbones to develop where jaw development did not occur during childhood.

SUMMARY OF THE INVENTION

The present invention is directed to a method for changing the form of the jaw and facial bones of a patient that did not develop fully during childhood by intermittently applying force to the bones through a device that translates the functional actions of the patient, such as swallowing, into the necessary force, allied with spatial changes associated with the overlay of the appliance/device.

In accordance with a presently preferred exemplary embodiment of the present invention, the method utilizes a device or appliance having a plate body that fits within the mouth of the patient. The plate may be in two halves connected by an expansion screw. Flap springs project from the plate body and an overlay extends from the plate body. Clasps with archways are also connected to the plate.

In practicing the method, the appliance is placed within the mouth of the patient, e.g., at night. It can be shaped to fit the lower jaw (mandible) or upper jaw (maxilla). In either case, the archway of each clasp is selectively placed about a tooth to hold the appliance in place. In this position the overlay extends over a tooth and prevents the jaws from fully closing. Initially, the overlay is placed on the patient's underdeveloped side. The flap springs press against selected teeth that are out of alignment in order to urge those teeth back into place. The unilateral vectors of force on the tooth's periodontium cause the jawbone to expand to accept the teeth in their proper position. Also, the device is arranged such that the patient's facial muscles are caused to intermittently pull on the facial bones when the opposing teeth contact the overlay during swallowing. This intermittent application of force to the facial bones causes these bones to further develop toward a symmetrical appearance of the face, and positions out of place teeth into proper positions. It is believed that the development of the bones into a symmetrical shape is due to the functional matrix effect.

The plate body halves of the device can be adjusted toward or away from each other by a small micro-motor connected to, or embodying the expansion screw. Further, the position of the flap springs, and thus the force they apply to the teeth, can also be adjusted by the same motor due to the movement of the body halves, or by one or additional micro-motors attached to the flap springs. Sensors may be applied to the flap springs so that the amount of force applied by these springs, either because of their motor or the separation of the body plate halves, can be determined. Further, a microprocessor can be located on the body plate and used to interpret the sensor readings. Further, the microprocessor can adjust the expansion screw motor and/or the flap spring motors based on the sensor readings, e.g., to keep the pressure even. Further, the dental health care professional can design a force pattern to be applied by the device to achieve the desired results. This pattern can be stored as predetermined parameters in a memory associated with the microprocessor, and used by the microprocessor with the sensor readings to adjust the motor or motors.

DESCRIPTION OF THE DRAWING FIGURES

These and other features, aspects, and advantages of the present invention will become better understood with reference to the following description, appended claims and the accompanying drawings wherein:

FIG. 1 is a top plan view of a device in accordance with the present invention;

FIG. 2 is a top plan view of a device in accordance with the present invention, which is located in conjunction with the upper teeth of a patient at the beginning of treatment and may be used to develop the jawbone and facial bones, and align the teeth of the patient;

DETAILED DESCRIPTION OF THE PRESENTLY PREFERRED EXEMPLARY EMBODIMENTS

Figure 3:
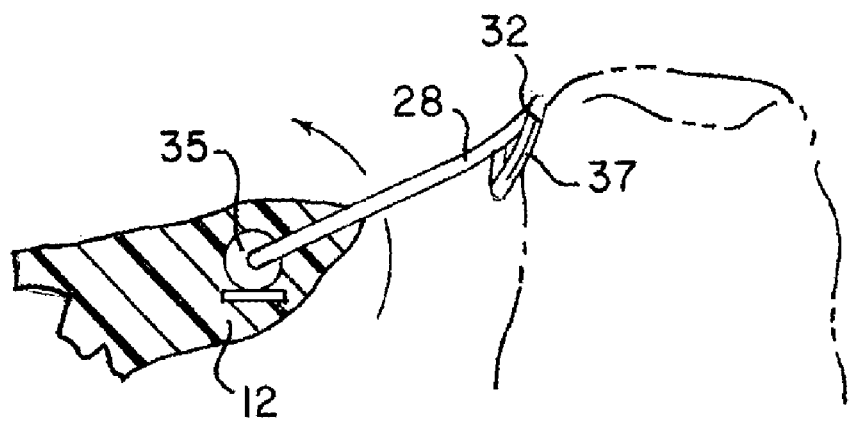
FIG. 3 is a cross-sectional view of the device of FIG. 2 along line 2-2.

Referring to FIGS. 1-3, there is shown an orthodontic device or appliance 10 of the split palate type in accordance with the present invention. Device 10 includes a plate body 12, preferably of plastic material, such as acrylic. The plate body is preferably in two halves 12A, 12B, but it can be in one piece or in several pieces of unequal size. Plate body 12 has an overlay 14 extending from it to a position that would cover the top of a tooth. While it is shown with one such overlay 14 on the left side in FIG. 1, it should be understood that the overlay may be on the right side and/or the left side. The location of the overlay is based on a clinical determination by the dental health care provider as to which facial muscles should be stressed more to achieve the desired result in an optimal way or how much stress should be applied. Typically more stress is applied to the muscles on the side where the overlay is located. As a result the overlay should be on the side where the facial and jawbones did not fully develop during childhood. Additionally, multiple overlays including more than one on each side of the device may be used.

A first clasp 16 and a second clasp 18 are connected to the plate, preferably by being embedded in the plastic material of plate body 12. Each clasp 16, 18 includes an archway 20, 22 for selectively permitting device 10 to be fitted about a tooth, preferably one of the posterior teeth, to hold the device or appliance in place. When fitted or connected, overlay 14 may be positioned to extend over one of the archways (archway 20 is shown in the FIG. 1, but overlay 14 could additionally or alternatively extend over archway 22) so as to be in contact with the tooth. Overlay 14 is preferably placed on top of the tooth adjacent to the archway 20 or 22 of the respective clasp 18, 20, thereby preventing the jaw from fully closing.

The halves 12A, 12B of plate body 12 may be connected by an expansion jack screw 24. While the screw 24 may be manually adjustable to control the separation of the plate halves, a small electrical micro-motor 25 may incorporate the screw 24 and be used to adjust the separation.

A Hawley frame 26, in the form of an arch wire, is also connected to the plate body 12, preferably by being embedded in the plastic material of the plate body 12. Hawley frame 26 wraps around the front of the teeth and additionally acts to kept the device 10 in place.

A plurality of flap springs 28, which are known in the art as Fisher flap springs, are connected to the plate body, preferably by being embedded in the plastic material of the plate body 12. Each flap spring is T-shaped, I-shaped or L-shaped including a tag portion 30 and a tooth supporting portion 32. Some of the tooth supporting portions 32 extend for a distance equal to at least the width of two teeth (see FIGS. 2 and 3). As is common, the tooth support portion 32 rests against the inside of the teeth and applies pressure at that location. Typically, the amount of pressure can be adjusted by manual bending of the tag portions 30.

As an alternative, small electrical motors 35 can be located between the body plate 12 and one or more of the flap springs 28 to adjust the pressure that the flap springs apply to the teeth without having to manually bend the springs. In addition, sensors 37 can be located at the ends of the flap springs where they meet the teeth in order to measure the pressure applied to each tooth or group of teeth by the flap spring. The sensor 37 can be located in other positions, but in such a case it would not provide a direct measurement of the pressure and some calculation would be necessary to arrive at the actual pressure.

During use of the device, as the jaw expands and other bones develop, it will be necessary to adjust the separation of the body plates 12A, 12B, as well as the force of the flap springs, in order to continue the development of the bones. This can be accomplished during periodic visits, e.g., once a week, to the dental health care provider for adjustments. Such adjustments can be manual or, where the motors 25, 35 are present, they can be made by applying an electric current to the motors. In part, these adjustments by the dental health care provider can be assisted by the provider reading the output of sensors 37.

A microprocessor 40 can be provided on or embedded within the body plate 12. In order to power the microprocessor, a battery 42 would also be provided. The microprocessor may be supplied via conducting wires with information from the sensors 37 and its output can drive the micro-motors 25, 35, via other conducting wires at least partially embedded in the plastic body 12, in order to automatically keep the pressure on the teeth at a preset level. In this way patient errors such as missed, over-zealous or reversed screw-turns are eliminated, and the visits to the dental health care provider are reduced to an optimized level. Further, the dental heath care provider can create a force profile that will lead to a good outcome for the patient. For example, the force vectors need to be long-acting, low-level and consistent so as not to over do the application of force and produce an inferior result. This profile may be in the form of data or digital codes stored in a memory that is part of the microprocessor. Thus the microprocessor would control the motors based on the profile data and the readings from the sensors.

By definition, the plate body 12 does not include the clasps 16, 18, the Hawley frame 26 and the flap springs 28. The body 12 of device 10, except for the overlay 14, is spaced from the patient's tissue, including the palate and mandibular lingual areas. Therefore, the only portion of the plate body 12 that touches the patient's tissue is the overlay 14, which contacts the biting (occlusal) surface of at least one of the patient's teeth in the space where that tooth would normally contact an opposing tooth from the opposite set of teeth, i.e., upper or lower jaw. Overlay 14 is sufficiently thick to prevent the jaws from fully closing. The thickness of the overlay, where it contacts the tooth preferably ranges from approximately 0.5 mm to approximately 15 mm. More preferably, the overlay has a thickness ranging from approximately 1.0 mm to approximately 6.0 mm. Most preferably, the thickness of the overlay ranges from approximately 2.0 mm to approximately 4.0 mm, with about 2.0 mm being preferred. The plate body 12 itself has a thickness that varies and ranges from about 2 mm to about 6 mm.

To change the form of the jaw and facial bones with device 10, the device is placed within the mouth of a patient so that overlay 14 contacts at least one tooth and the remainder of the plate body 12 is spaced from the patient's tissue, including the palate. Overlay 14 prevents the patient's jaws from fully closing. It is believed that this contact of the teeth with the overlay causes intermittent force to be applied to the body plate 12 and through it to the flap springs 28 to the teeth. It further causes the patient's jaw and facial muscles to stimulate the facial and alveolar bones during function, essentially each time the patient swallows, which is estimated to be about 2,000 to 3,000 times per day. This frequent pulling on the facial and alveolar bones is believed to cause development of the facial and jaw bones where jaw development did not fully occur during childhood. This bone development may include a descent of the palate (i.e., remodeling of the vault of the palate downwardly toward the lower jaw), if necessary.

Figure 4:
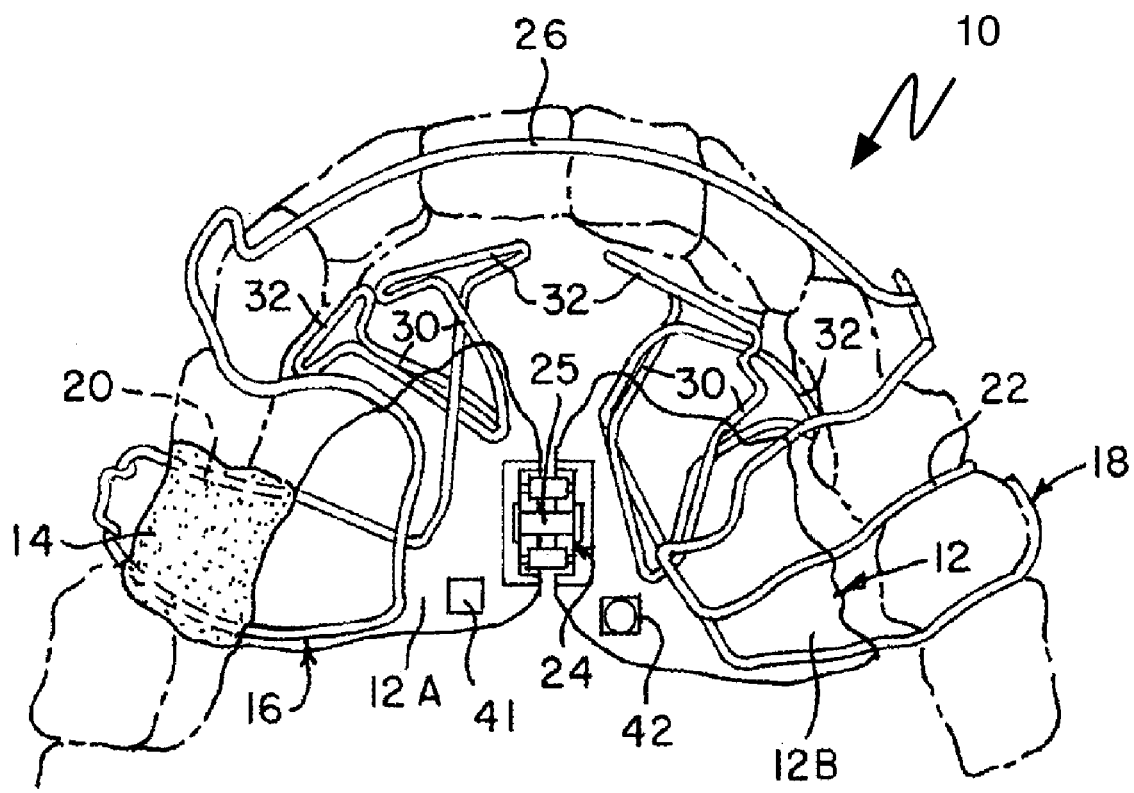
FIG. 4 is a top plan view of the device of FIG. 2 placed in the patient's mouth after partial treatment.

Assuming FIG. 2 shows the device of the present invention when initially used with a patient at the beginning of treatment, FIG. 4 is the same view of the device 10 after partial treatment. It should be noted that the teeth have been pressed outwardly in FIG. 4 compared to that in FIG. 2. In effect the jawbone has been expanded to accommodate the new position of the teeth.

Figure 5:
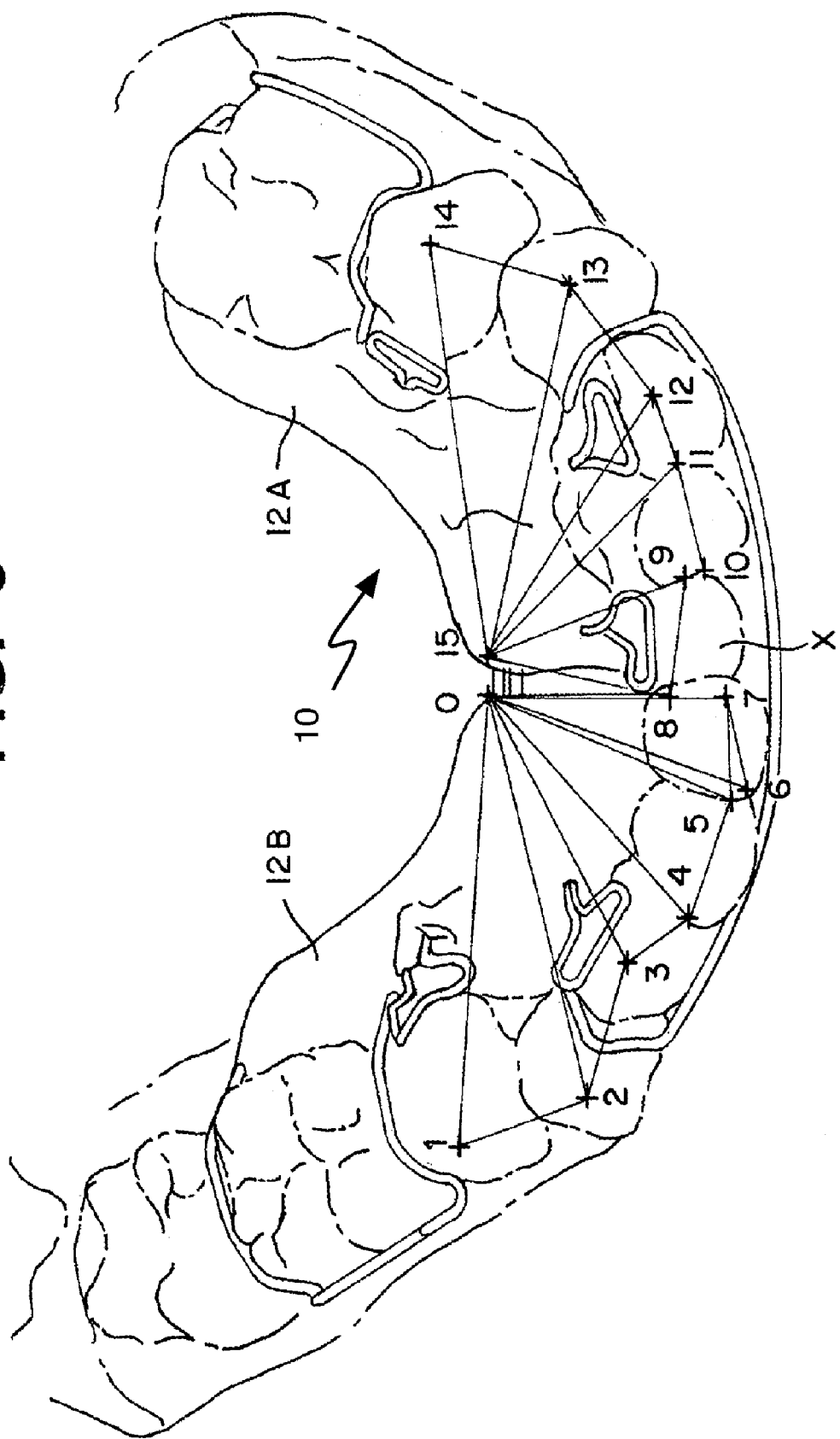
FIG. 5 is an illustration of the lower teeth in a patient's mouth at the beginning of treatment showing the placement of the device and a diagram of the alignment of the patient's teeth.
Figure 6:
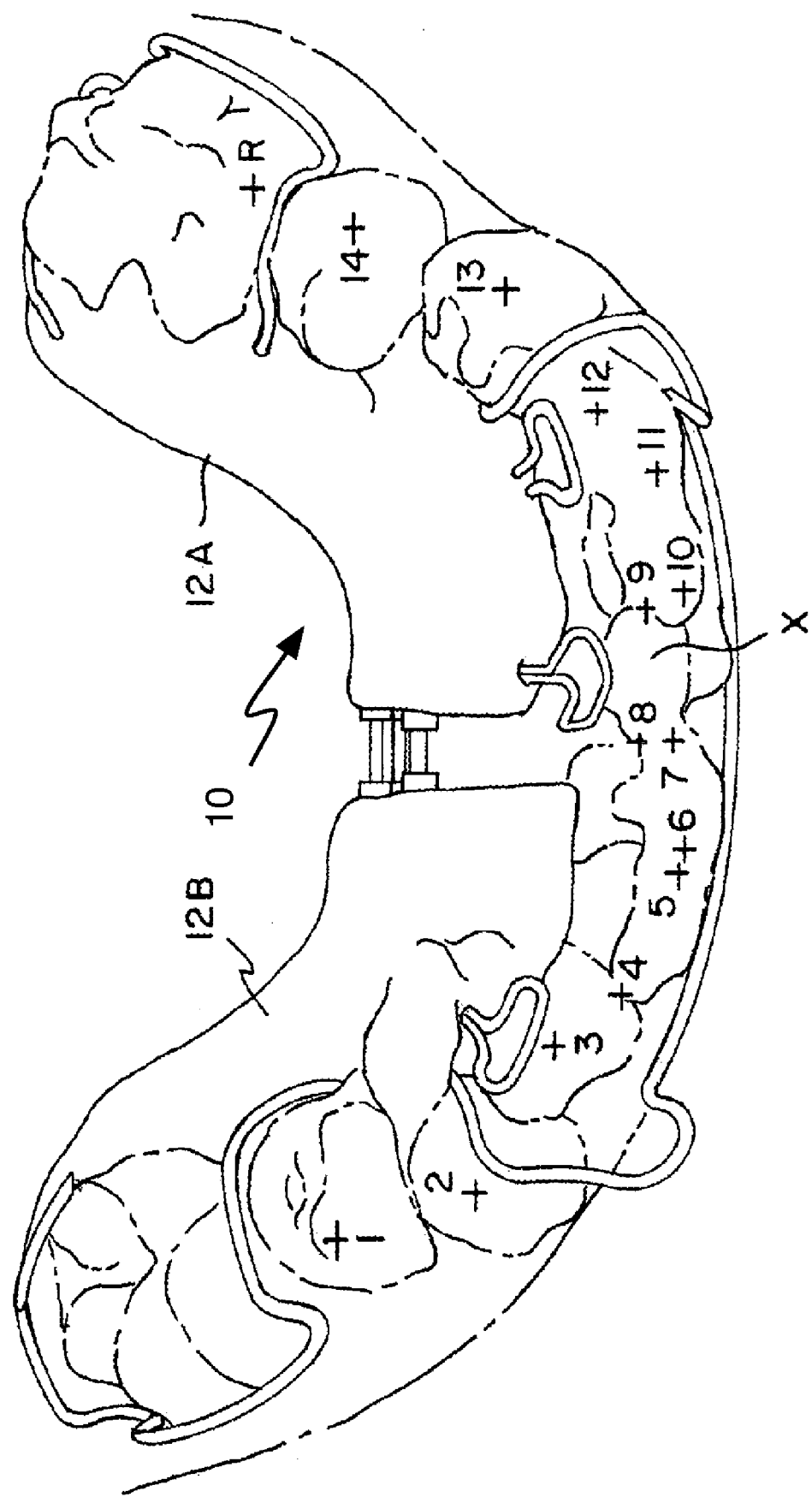
FIG. 6 is an illustration of the lower teeth in a patient's mouth after partial treatment showing the placement of the device and a diagram of the alignment of the patient's teeth at that point in the treatment.

FIG. 5 is a view of the teeth of a patient at the beginning of treatment showing the placement of the device and a diagram of the alignment of the patient's teeth. Notice that tooth X is out of alignment and there is not enough room between adjacent teeth for it to be properly aligned. FIG. 6 is similar to FIG. 5, but at a time after partial treatment of the patient. Notice that tooth X is now better aligned because more room has been provided between the adjacent teeth because of the effect of the device 10.

Marked on the illustration of FIG. 5 is a diagram of the alignment of the teeth. Using specific landmarks, reference lines (finite-elements) are drawn from location "0" on body plate half 12A and from location 15 on body plate half 12B to the teeth. The finite-elements are drawn to locations (landmarks) on the teeth, which are toward their front surfaces at about the mid points with regard to locations 1, 2, and 3 on body plate half 12A, as well as to locations 12, 13 and 14 on body plate half 12B. These represent teeth that are already in alignment. As regards the teeth to be aligned, similar finite-elements are drawn to the edges of each tooth, e.g., to locations 4, 5 for one tooth and 6, 7 for the other tooth from body plate 12A. Similarly, lines are drawn to locations 8, 9 and 10, 11 for the teeth contacted by the flap springs from plate body half 12B. Thus, specific landmarks are used to identify regions of the teeth and the device. By subjecting these specific landmarks to finite-element analysis, localization and quantification of changes in shape, size and direction of the spatial arrangements of the teeth and the device are computed, using a method developed by Singh et alia (Morphometry of the cranial base in subjects with Class III malocclusion. Journal of Dental Research, 76(2): 694-703, 1997).

Figure 7:
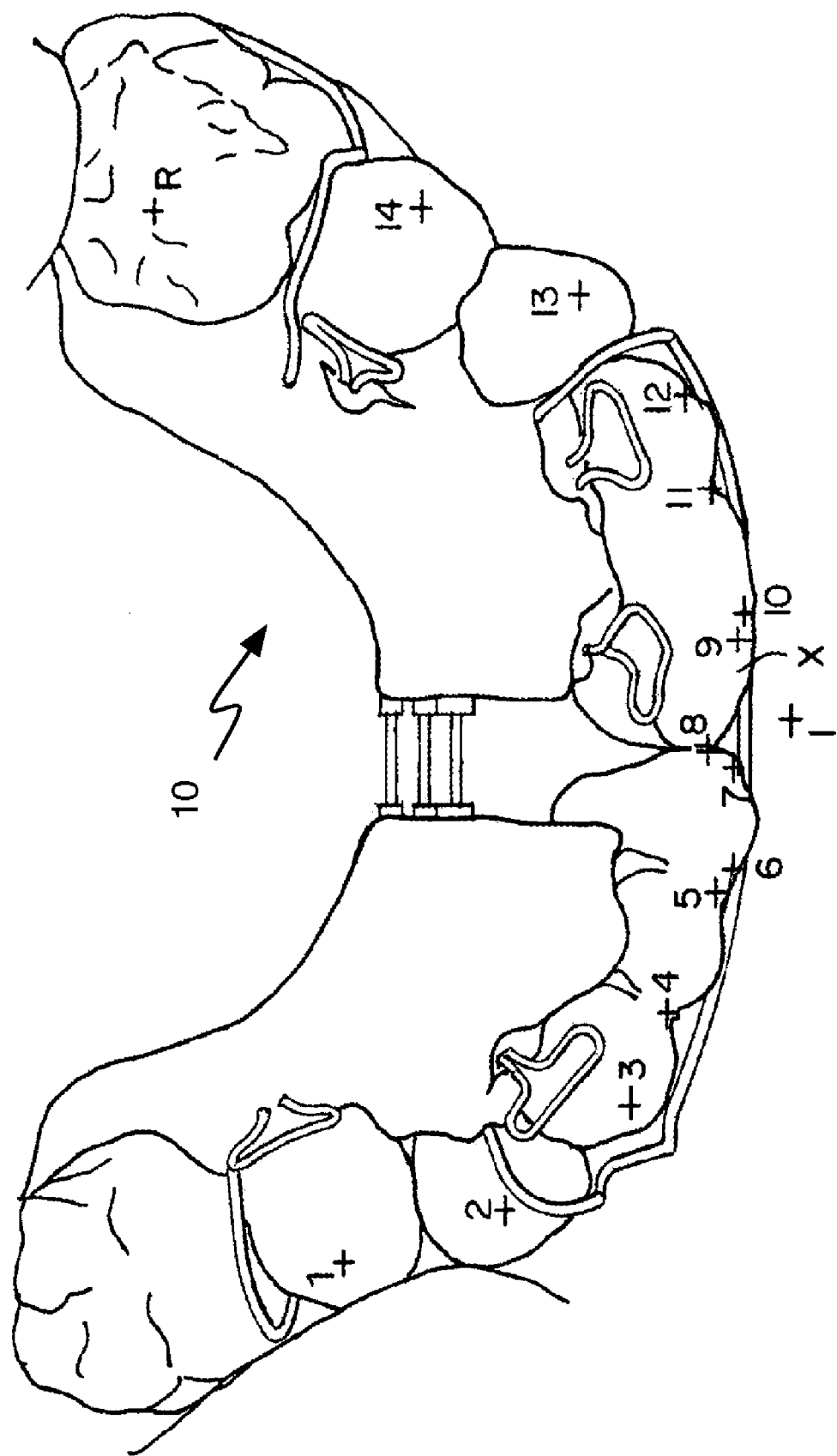
FIG. 7 is an illustration of the lower teeth in a patient's mouth near completion of treatment showing a diagram of the alignment of the patient's teeth at that point in the treatment.
Figure 8:
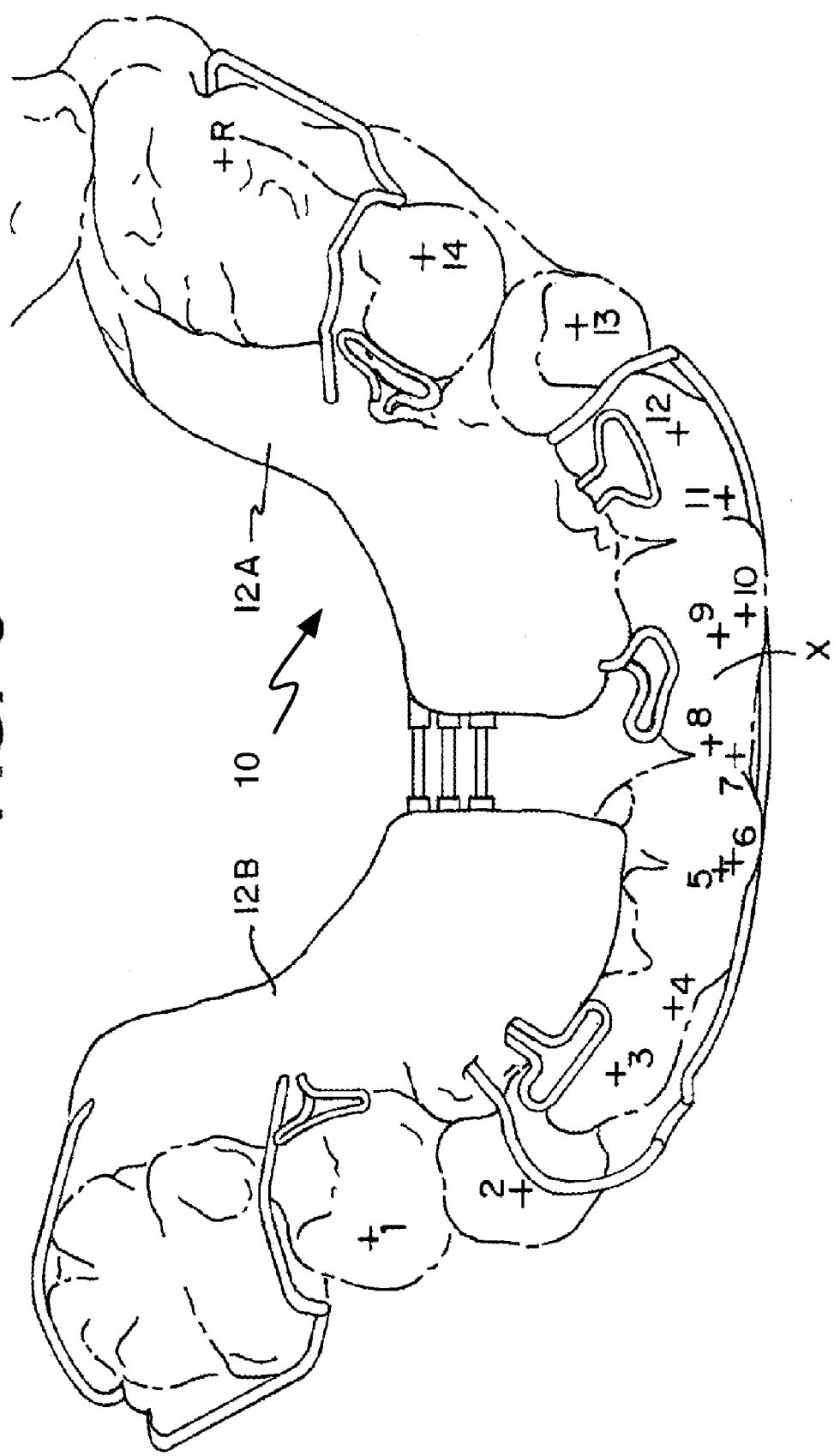
FIG. 8 is an illustration of the lower teeth in a patient's mouth after full treatment showing a diagram of the alignment of the patient's teeth at the end of treatment.
Figure 9:
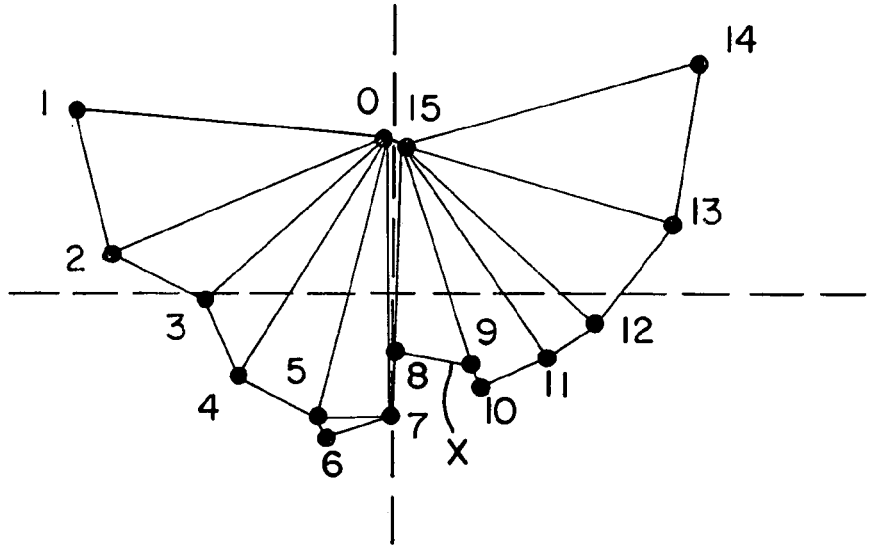
FIGS. 9-13 are diagrams of finite-elements of the teeth as marked in FIGS. 5-8 showing the progression of alignment of the teeth due to the device.
Figure 10:
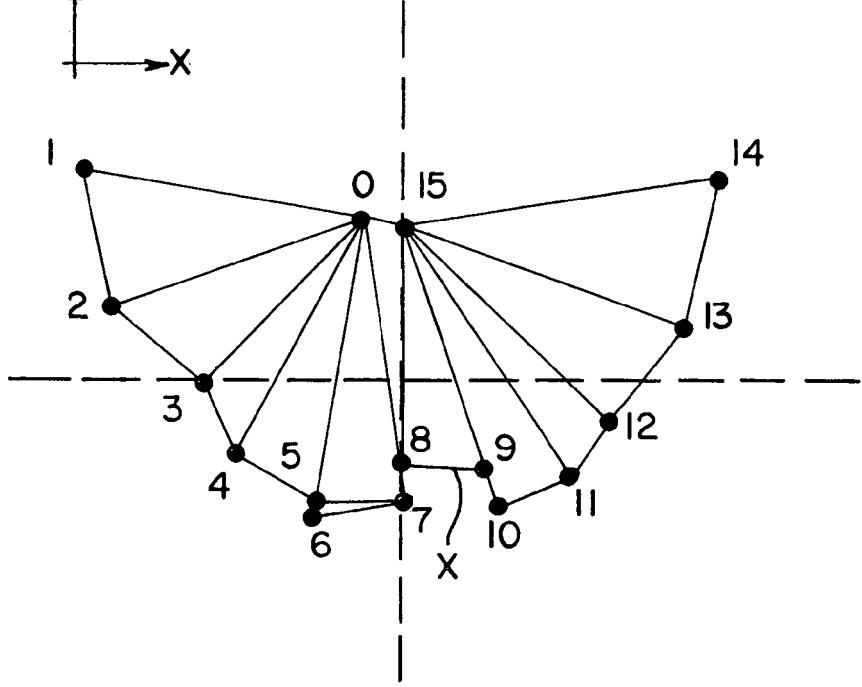
Figure 11:
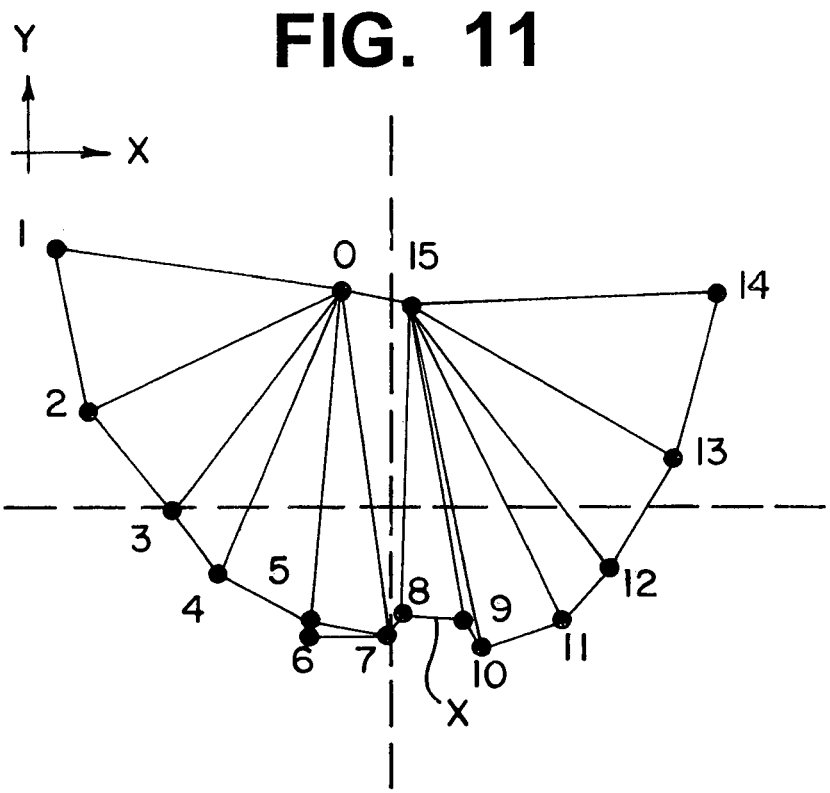
Figure 12:
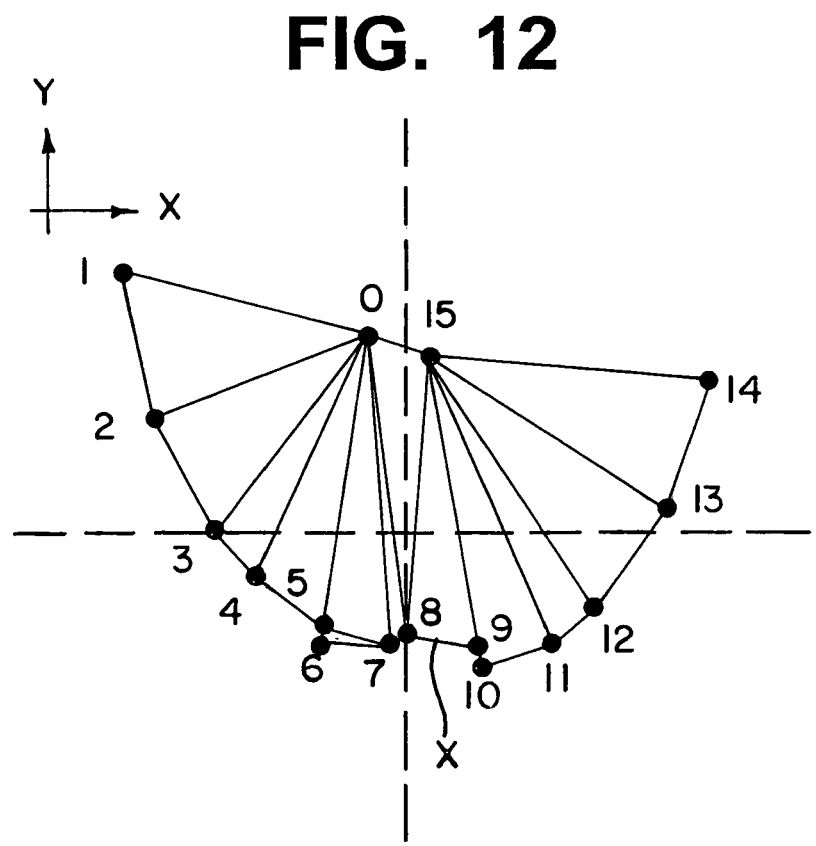
Figure 13:
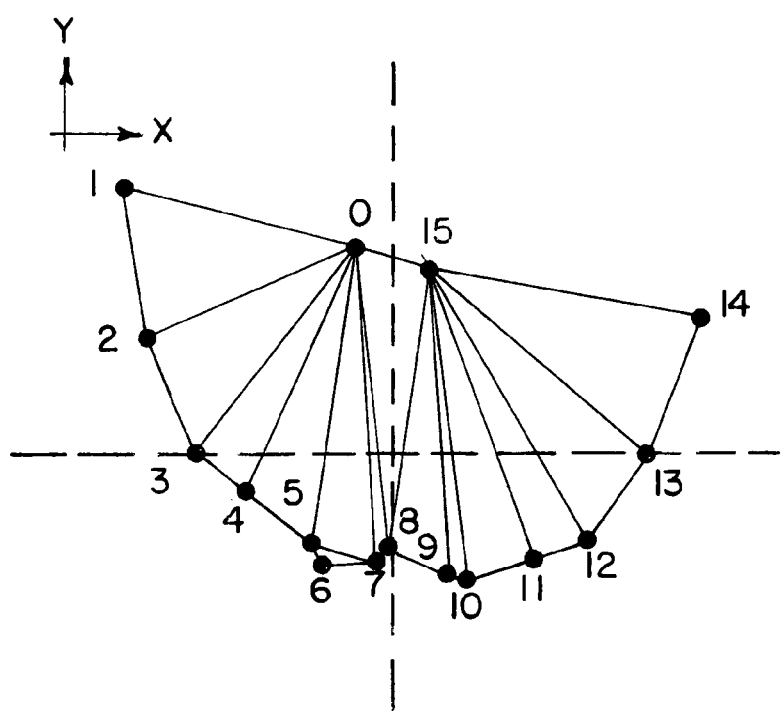

FIG. 7 shows the same patient about six (6) months later after wearing the device, essentially for at least four waking hours per day and while sleeping approximately eight hours per night. Notice that tooth X is nearly aligned. Finally, in FIG. 8 the arrangement of the teeth is shown at the end of treatment with tooth X properly aligned with the rest of the teeth. Throughout the process shown in FIGS. 6-8, the patient's jawbone has expanded in size, probably due to bone remodeling in the palatal region, and the teeth have been moved into new and properly aligned positions.

FIGS. 9-13 are diagrams of the teeth as marked in FIGS. 5-8 showing the progression of alignment of the teeth due to the device. These diagrams can be plotted in a graphics program such as Morpho Studio, e.g., version 2.0 or higher. This set of diagrams particularly shows the movement of tooth X. As this response is typical of use of the invention, the diagrams of FIGS. 9-13 can be used to create a force profile, which would indicate the preferable force to be applied along each segment of the diagram at particular points in time in order to produce an acceptable result in the shortest period of time. When a microprocessor controlled device is used, this profile can be incorporated into the program of the microprocessor to apply force over time to the teeth in this manner.

Figure 16:
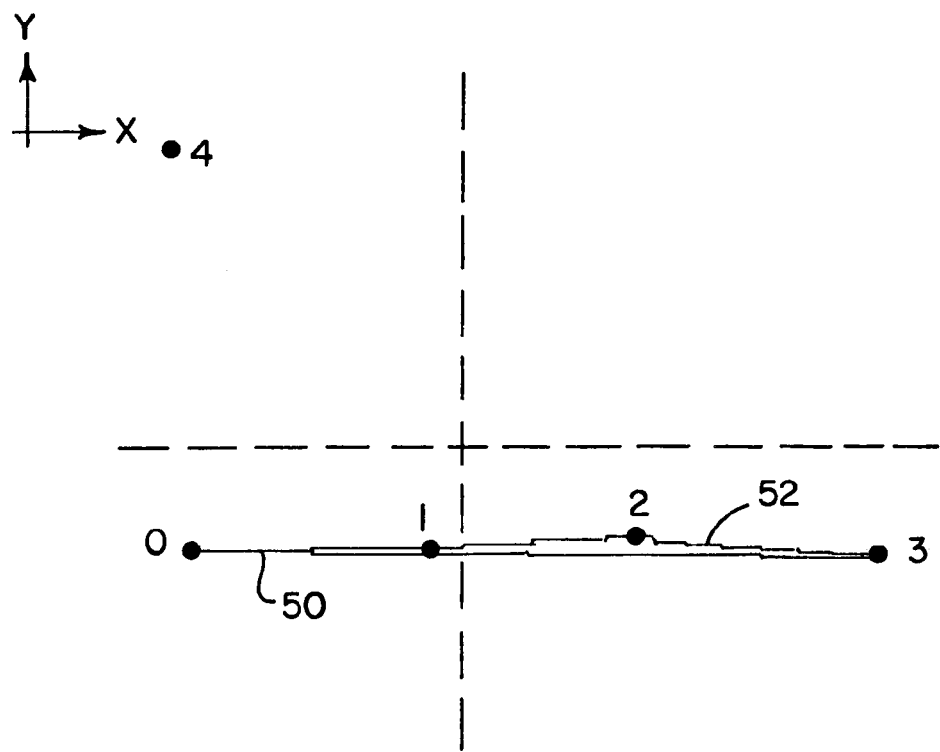
FIG. 16 is a diagram of the x, y coordinates of the eye alignment in FIG. 14 showing an under developed face.
Figure 14:
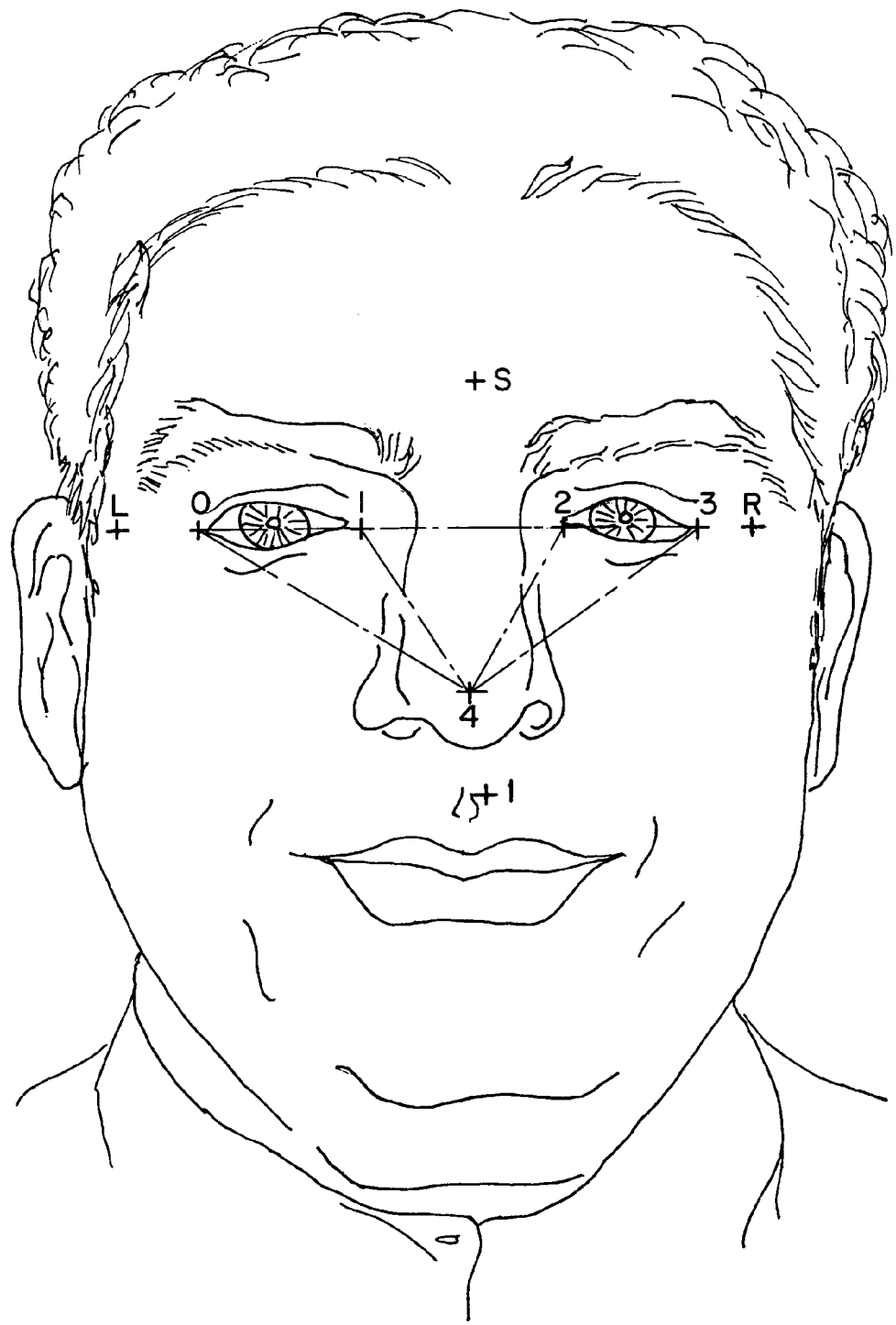
FIG. 14 is a reproduction of a photograph of a patient's face at the beginning of treatment showing a diagram of the alignment of the eyes.

FIG. 14 is an illustration of a patient's face at the beginning of treatment showing a diagram of the alignment of the eyes. Line 50 shows the alignment of the patient's eye on the left side of the illustration and line 52 shows the alignment of the patient's eye on the right side. The angle between the eyes is labeled 54. As can be seen, this angle 54 is noticeably less than 180 degrees, which would indicate perfect symmetry. FIG. 16 is a computer generated diagram of the lines 50, 52, which shows their relationship in more detail because the facial features are not present.

Figure 15:
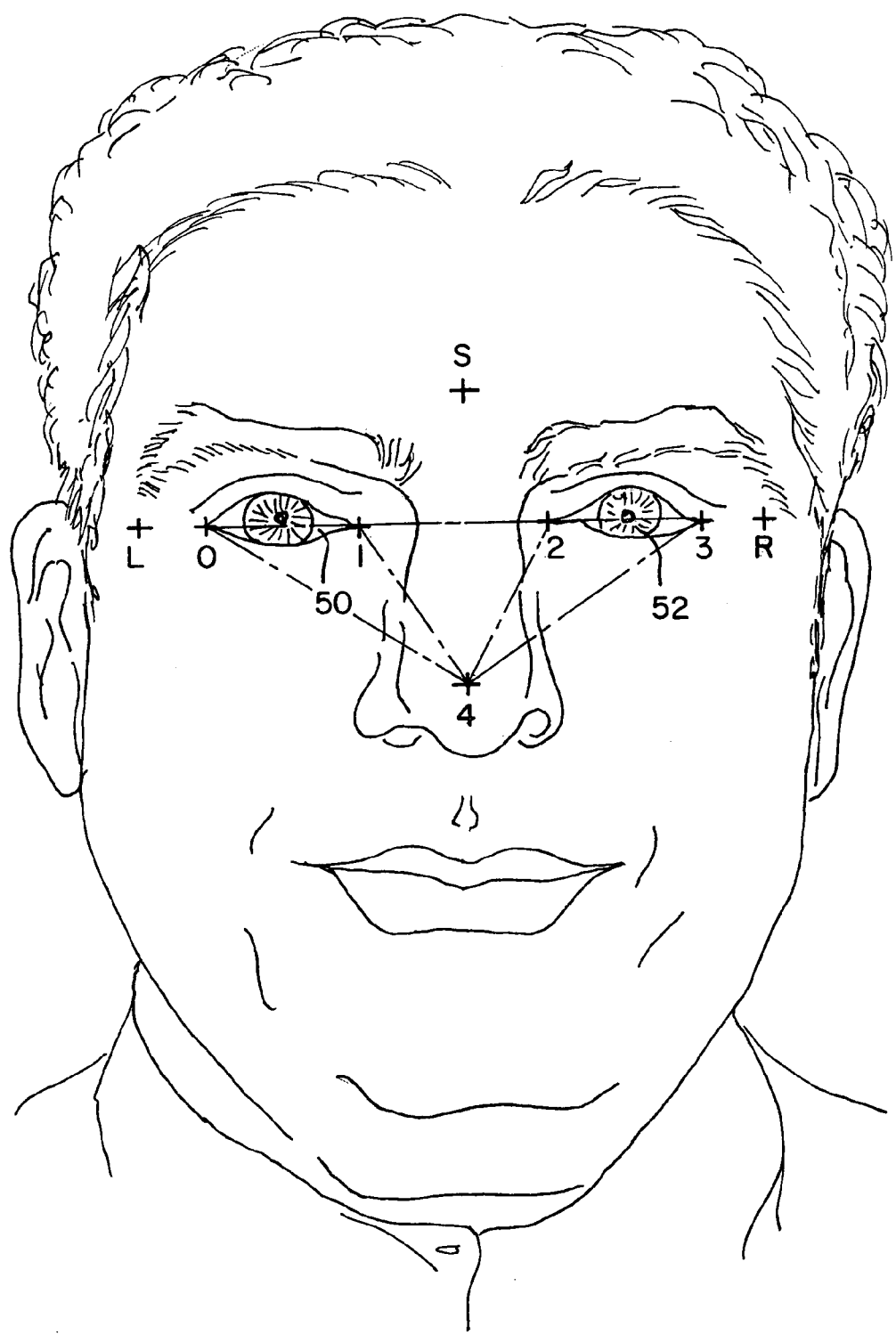
FIG. 15 is a reproduction of a photograph of the patient's face shown in FIG. 14 after full treatment showing a diagram of the alignment of the eyes and the symmetrical nature of the face.
Figure 17:
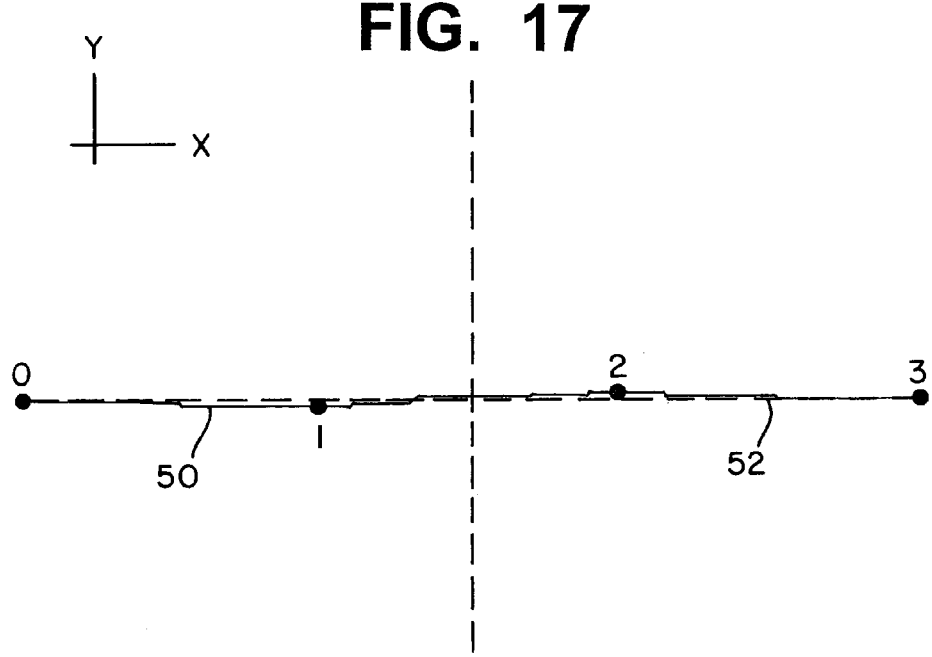
FIG. 17 is a diagram of the x, y coordinates of the eye alignment in FIG. 15, showing a developed symmetrical face.

FIG. 15 is an illustration of the face of the same patient shown in FIG. 14 after full treatment with the device according to the invention. As can be seen, the angle 54 is now almost 180 degrees, which indicates the alignment of the eyes and the symmetrical nature of the face. FIG. 17, which is a computer generated diagram of lines 50, 52 shows the alignment in more detail.

Figure 18:
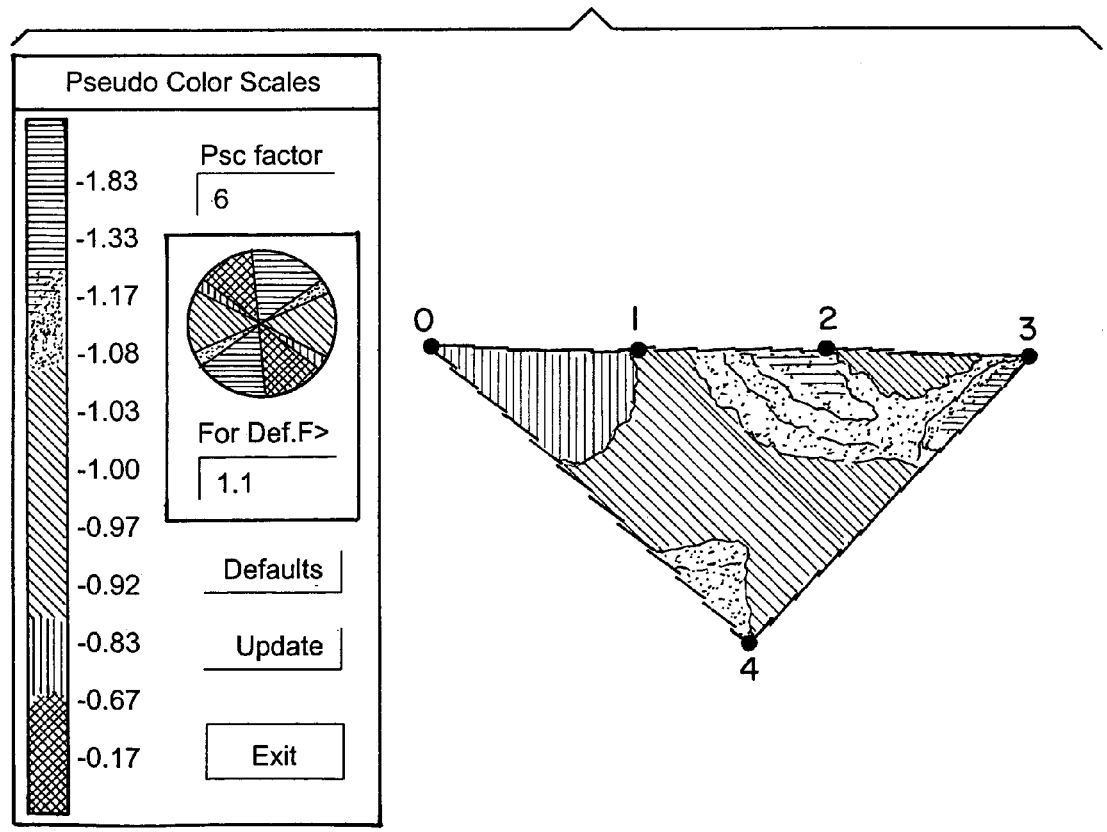
FIG. 18 is a diagram of finite-element analysis, showing the change in facial bone development from that of the patient in FIG. 14 to that in FIG. 15.

FIG. 18 is a diagram showing the change in facial bone development from that of the patient in FIG. 14 to that in FIG. 15, using finite-element analysis. In the diagram, the point 0 is at the outside corner of the eye of the patient on the left side of the illustration in FIGS. 14 and 15, while point 3 is at the outside corner of the eye on the right side of the illustration. Point 4 is at the tip of the patient's nose in FIGS. 14 and 15. The shaded areas of the diagram show the size increase and the cross hatched areas indicate the size decrease. The application of force would be expected to create a decrease in the bone mass, but not an increase. Thus, there is a remodeling of the patient's face that is not completely explainable by mere application of force. This diagram can be produced by Morpho Studio software, version 2.0 or higher.

In each of FIGS. 5-18, it can be seen that the use of device 10 caused a remodeling or reshaping of the face and jawbones thereby creating better facial symmetry. This remodeling of the bones resulted in at least one of higher cheekbones, stronger jaw appearance and a wider smile, facial features that society usually equates with a pretty or handsome face.

This alignment was brought about by the application of intermittent force to the tissues of the face. During function, e.g., as the patient swallows while wearing the device, either while awake or asleep, the teeth come into contact with the overlay 14, which applies force to the face muscles and through the device to the bones of the jaw. This repetitive force causes deformation of the bones of the jaw and face. While not wishing to be held to any theory of operation, it is believed that the symmetrical nature of the result of the reformation of the jaw and facial bones is not due entirely to the application of force to specific areas of bone, but to the genetic code of the patient as predicted by the functional matrix hypothesis of Moss.

Figure 19:
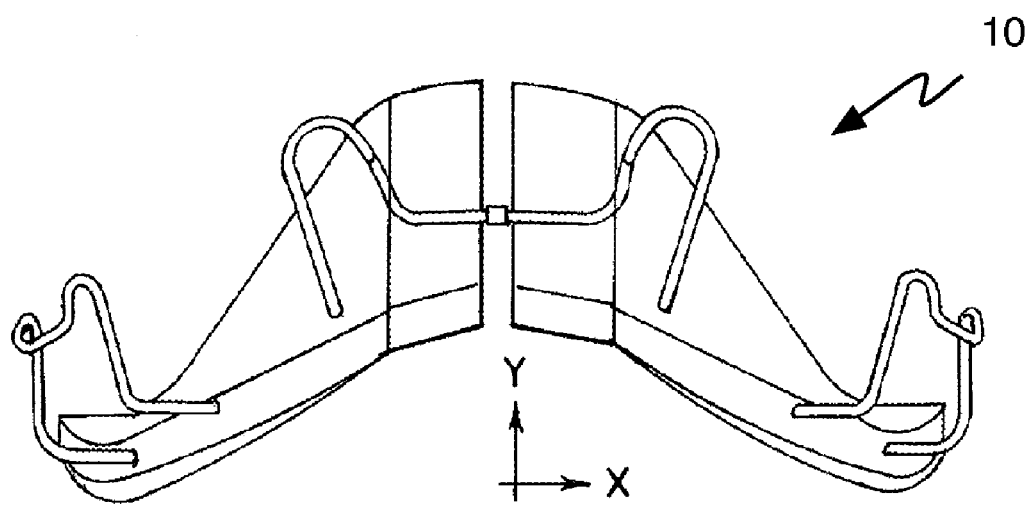
FIG. 19 is a front elevation view of a computer model of the appliance according to the present invention.
Figure 20:
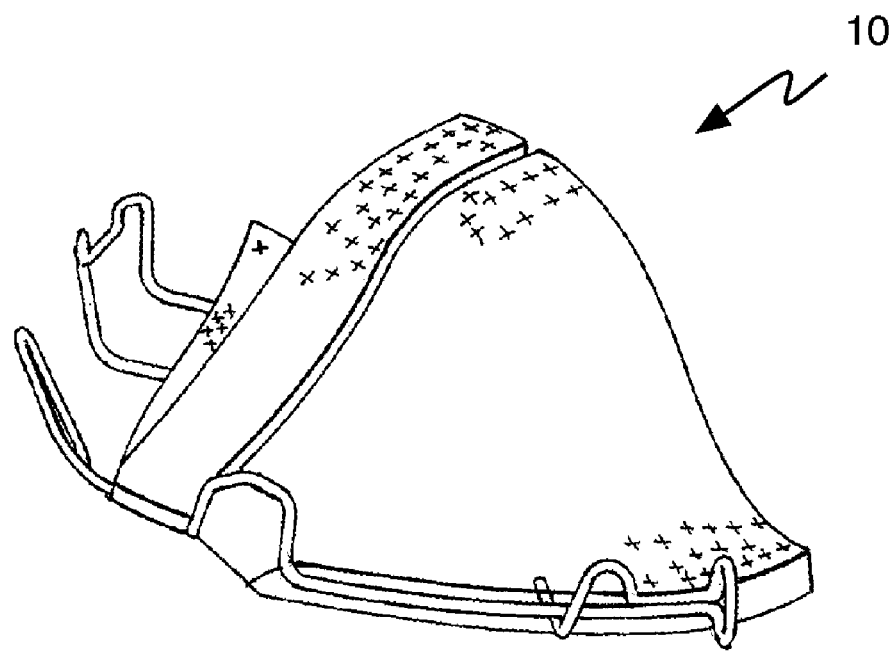
FIG. 20 is a perspective view of a three dimensional finite-element model of the present invention.

FIGS. 19 and 20 illustrate a stylized and a simplified three dimensional virtual computer model of the device. In particular, FIG. 20 is a finite element model. Its entire surface is covered with finite elements (or reference points), each indicated with a small "x." However, in the drawing, only some of the finite elements are shown for simplicity. Computer modeling as shown in FIGS. 19 and 20 can be used to analyze the function of the device and to test various configurations. This is particularly true with respect to the effects of the overlay and plate, as well as automatic control of micro-motors. As a result of such modeling, the testing of a new device can be reduced, thus reducing the time to market the product. Further, it is possible to use the device model in conjunction with models of the human face, to predict the response to muscle action and the correction of facial distortions with various designs of the appliance, according to the functional matrix hypothesis of Moss.

Having described the presently preferred exemplary embodiment of an orthopedic and orthodontic device in accordance with the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims.

What is claimed is:

1. A method for changing the form of at least one of the facial and jaw bones of a patient in which such bone did not develop fully during childhood, said method comprising the steps of: providing a device having a plate body that fits within the mouth of the patient, flap springs that project from the plate body and an overlay extending from the plate body; placing the device within the mouth of the patient so that the overlay is in a position between at least an upper and lower tooth of the patient, the flap springs press against at least one selected tooth that is out of place and the plate body is spaced from the patient's tissue, including the palate; and arranging the shape and placement of the device such that contact of the patient's upper tooth and lower tooth or teeth with the overlay causes the patient's facial muscles to intermittently pull on at least one of the bones essentially each time the patient swallows, thereby causing further development of the at least one bones toward a symmetrical appearance of the face and the positioning of the out of place tooth or teeth into a proper position or positions.

2. The method according to claim 1, further comprising the step of placing said overlay only between teeth on one side of the patient's mouth.

3. The method according to claim 2, wherein said overlay is placed on a side of said patient's mouth corresponding to the side where at least one of the bones did not fully develop during childhood.

4. The method according to claim 1, further comprising the step of placing said overlay between teeth on both sides of the patient's mouth.

5. The method according to claim 1, wherein said flap springs cause the jawbone of the patient to expand to accommodate an out of place tooth or teeth.

6. The method according to claim 5, wherein the plate body is in two pieces connected by a motorized screw to bring the halves together or moving them apart, and further comprising the step of operating the screw motor periodically to adjust the spacing between the plate body halves to compensate for expansion of the jawbone.

7. The method according to claim 6, wherein the device further includes sensors to detect the pressure applied to the tooth, and further comprising the step of determining the pressure on the tooth by reading the sensors and the step of operating the screw motor based on the pressure readings.

8. The method according to claim 7, wherein the device further includes a processor that reads the sensor and controls the screw motor, and wherein the step of operating the screw motor is carried out by the processor based on the sensor readings and predetermined parameters.

9. The method according to claim 5, wherein the plate body is in two pieces connected by a motorized screw for bring the halves together or moving them apart, wherein the device further includes sensors for sensing the pressure applied to the tooth, a micro-motor located between the plate body and the flap spring for controlling the pressure applied by the flap spring, and a processor that reads the sensor and controls the screw motor and the micro-motor, and further comprising the steps of: determining the pressure on the tooth by the processor reading the sensors;

and causing the processor to operate at least one of the screw motor and micro-motor periodically to adjust the spacing between the plate body halves to compensate for expansion of the jawbone and to adjust the pressure on the tooth by the flap spring.

10. The method according to claim 1, wherein the device further includes a micro-motor located between the plate body and the flap spring for controlling the pressure applied by the flap spring, and further comprising the step of operating the micro-motor periodically to adjust the pressure on the tooth by the flap spring.

11. The method according to claim 10, wherein the device further includes sensors to detect the pressure applied to the tooth, and further comprising the step of determining the pressure on the tooth by reading the sensors and the step of operating the micro-motor based on the pressure readings.

12. A device comprising: a plate body in the form of two halves and designed to fit within the mouth of a patient; an overlay extending from at least one of the plate body halves, said overlay being designed to fit between at least an upper tooth and an opposing lower tooth of the patient so the patient's mouth cannot fully close; a clasp connected to said plate body, said clasp selectively connecting said device to at least one tooth of a patient; a motorized screw connection between the halves of the plate body to move the halves toward or away from each other; at least one flap spring connected to said plate body and designed to contact and apply pressure to at least one tooth of the patient; and at least one sensor located on the flap spring and measuring the pressure applied to the tooth by the flap spring.

13. The device according to claim 12, wherein said plate body is spaced from the patient's tissue, including the palate.

14. The device according to claim 12 further comprising a pressure control device that varies the pressure applied to the tooth by the flap spring.

15. The device according to claim 12, wherein said flap spring is T-shaped including a tag portion connected to the plate body and a tooth supporting portion contacting at least one tooth, said tooth supporting portion extending for a distance equal to at least the width of two teeth.

16. The device according to claim 12, wherein said plate body is made of plastic, including but not restricted to fabrication by reverse engineering.

17. The device according to claim 16, wherein said plastic is acrylic.

18. The device according to claim 12, wherein said overlay, at least in the area where it contacts said tooth, has a thickness ranging from approximately 0.5 mm to approximately 15.0 mm.

19. The device according to claim 18, wherein said overlay, at least in the area where it contacts said tooth, has a thickness ranging from approximately 1.0 mm to approximately 6.0 mm.

20. The device according to claim 19, wherein said overlay, at least in the area where it contacts said tooth, has a thickness ranging from approximately 2.0 mm to approximately 4.0 mm.

21. The device according to claim 12, wherein said overlay is disposed solely on one side of said plate body.

22. The device according to claim 12, further comprising a second overlay, wherein said overlay is disposed on both sides of said plate body.

23. The device according to claim 12, wherein said clasp includes an archway extending around at least one of said posterior teeth.

24. The device according to claim 23, wherein said overlay extends over at least a portion of said archway.

25. A device comprising: a plate body in the form of two halves and designed to fit within the mouth of a patient; an overlay extending from at least one of the plate body halves, said overlay being designed to fit between at least an upper tooth and an opposing lower tooth of the patient so the patient's mouth cannot fully close; a clasp connected to said plate body, said clasp selectively connecting said device to at least one tooth of a patient; a motorized screw connection between the halves of the plate body to move the halves toward or away from each other; at least one flap spring connected to said plate body and designed to contact and apply pressure to at least one tooth of the patient; and a processor for reading a sensor to determine the pressure applied to the tooth by the flap spring and for operating a pressure control device to vary the pressure according to predetermined parameters.

26. The device according to claim 25 in which the processor is a microprocessor located on the plate body and the pressure control device is a micro-motor.

* * * * *